US006756205B2

(12) United States Patent
Smith et al.

(10) Patent No.: US 6,756,205 B2
(45) Date of Patent: Jun. 29, 2004

(54) METHODS FOR INHIBITING CGRP BINDING

(75) Inventors: Derek David Smith, Omaha, NE (US); Shankar Saha, Indianapolis, IN (US); Peter W. Abel, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 09/813,345

(22) Filed: Mar. 20, 2001

(65) Prior Publication Data

US 2002/0068814 A1 Jun. 6, 2002

Related U.S. Application Data

(62) Division of application No. 09/070,504, filed on Apr. 30, 1998, now Pat. No. 6,268,474.

(51) Int. Cl.$^7$ .............................................. G01N 33/53
(52) U.S. Cl. ........................ 435/7.1; 530/326; 530/300; 514/2
(58) Field of Search ............................. 435/71; 530/326

(56) References Cited

U.S. PATENT DOCUMENTS

| | | | |
|---|---|---|---|
| 4,530,838 A | 7/1985 | Evans et al. | |
| 5,503,989 A | 4/1996 | Bibbs et al. | |
| 5,580,953 A | 12/1996 | Albrecht et al. | |
| 5,625,032 A | 4/1997 | Gaeta et al. | |

OTHER PUBLICATIONS

Aiyar et al., "Differential Calcitonin Gene–Related Peptide (CGRP) and Amylin Binding Sites in Nucleus Accumbens and Lung: Potential Models for Studying CGRP/Amylin Receptor Subtypes", *J. Neurochem*. 65:1131–1138, 1995.
Aiyar et al., "Identification and Characterization of Calcitonin Gene–Related Peptide Receptors in Porcine Renal Medullary Membranes", *Endocrinology* 129:965–969, 1991.
Amara et al. "Alternative RNA processing in calcitonin gene expression generates mRNAs encoding different polypeptide products", *Nature* 298:240–244, 1982.
Beaumont et al., "Regulation of muscle glycogen metabolism by CGRP and amylin: CGRP receptors not involved", *Br. J. Pharmacol*. 115:713–715, 1995.
Bény et al., "Effects of substance P, calcitonin gene–related and capsaicin on tension and membrane potential of pig coronary artery in vitro", *Regulatory Peptides*, 25:25–36, 1989.
Bockman, C.S. et al., "Binding and Functional Characterization of Alpha–2 Adrenergic Receptor Subtypes on Pig Vascular Endothelium", *J. Pharmacol. Exp. Ther*. 267: 1126–1133, 1993.
Champion et al., "Adrenomedullin–(22–52) antagonizes vasodilator responses to CGRP but not adrenomedullin in the cat", *Am. J. Physiol*. 272:R234–242, 1997.
Collyear, K. et al., "Predicted structure of the bovine calcitonin gene–related peptide and the carboxy–terminal flanking peptide of bovine calcitonin precursor", *J. Mol. Endocrinol*. 6:147–152, 1991.

Cooper et al., "Amylin found in amyloid deposits in human type 2 diabetes mellitus may be a hormone that regulates glycogen metabolism in skeletal muscle", *Proc. Natl. Acad. Sci. USA* 85:7763–7766, 1988.
Deems et al., "Amylin or CGRP(8–37) Fragments Reverse Amylin–Induced Inhibition of $^{14}$C–Glycogen Accumulation", *Biochem. Biophys. Res. Commun*. 181:116–120, 1991.
Dennis, et al., "hCGRP$_{8-37}$, a Calcitonin Gene–Related Peptide Antagonist Revealing Calcitonin Gene–Related Peptide Receptor Heterogeneity in Brain and Periphery", *J. Pharmacol. Exp. Ther*. 254:123–128, 1990.
Eguchi et al., "Structure–Activity Relationship of Adrenomedullin, a Novel Vasodilatory Peptide, in Cultured Rat Vascular Smooth Muscle Cells", *Endocrinol*. 135:2454–2458, 1994.
Esneu et al., "Localization, Idenfication, and Acton of Calcitonin Gene–Related Peptide in the Frog Adrenal Gland", *Endocrinol*. 135:432–430, 1994.
Eysselein et al,. "Structural Characterization of Calcitonin Gene–Related Peptide Purified From Rabbit Intestine", *Peptides* 12:289–295, 1991.
Ezra et al., "Calcitonin gene–related peptide: a potent modulator of coronary flow", *Eur. J. Pharmacol.*, 137:101–105, 1987.
Feuerstein et al., "Clinical perspectives of calcitonin gene related peptide pharmacology", *Can. J. Physiol. Pharmacol*. 73:1070–1074, 1995.
Fisher et al., "Stimulation of noradrenergic sympathetic outflow by calcitonin gene–related peptide", *Nature*, 305:534–536, 1983.
Franc–Cereceda et al., "Calcitonin gene–related peptide but not substance P mimics capsaicin–induced coronary vascodilation in the pig", *Eur. J. Pharmacol*. 142: 235–243, 1987.
Gardiner et al., "Antagonistic Effect of Human α–Calcitonin Gene–Related Peptide (8–37) on Regional Hemodynamic Actions of Rat Islet Amyloid Polypeptide in Conscious Long–Evans Rats", *Diabetes* 40:948–951, 1991.
Griffin et al., "Effect of Endotoxicosis on Plasma and Tissue Levels of Calcitonin Gene–Related Peptide", *Circ. Shock* 38:50–54, 1992.
Huttemeier, et al., "Calcitonin gene–related peptide mediates hypotension and tachycardia in endotoxic rats", *Am. J. Physiol*. 265:H767–H769, 1993.
Jansz, et al., "Identification and Partial Characterization of the Salmon Calcitonin/CGRP Gene by Polymerase Chain Reaction", *Ann. N. Y. Acad. Sci*. 657:63–69, 1992.
Jian et al., "Calcitonin Gene–Related Peptide in the Pathogenesis and Treatment of Hypertension", *Chinese Medical Journal* 102(12):897–901, 1989.

(List continued on next page.)

*Primary Examiner*—Gary Kunz
*Assistant Examiner*—Dong Jiang
(74) *Attorney, Agent, or Firm*—Mueting, Raasch & Gebhardt, P.A.

(57) ABSTRACT

This invention relates to antagonists of calcitonin gene related peptide and in particular the invention relates to amino terminal modifications to peptides to improve their ability to bind to a member of the CGRP-receptor superfamily.

27 Claims, 6 Drawing Sheets

OTHER PUBLICATIONS

Joyce et al., "Calcitonin gene–related peptide levels are elevated in patients with sepsis", *Surgery* 108:1097–1101, 1990.

Kimura, S. et al., "Isolation and Amino Acid Sequence of Calcitonin Gene Related Peptide From Porcine Spinal Cord", *Neuropeptides* 9:75–82, 1987.

Kitamura et al., "Adrenomedullin: A Novel Hypotensive Peptide Isolated from Human Pheochromocytoma", *Biochemical and Biophysical Research Commuications*, 192:553–560 1993.

Leffert, J.D. et al., "Rat amylin: Cloning and tissue–specific expression in pancreatic islets", *Proc. Natl. Acad. Sci. USA* 86:3127–3130, 1989.

Ling et al., "Synthesis of Antigenic Determinant Tyr–CGRP=(27~37) of Calcitonin Gene–Related Peptide," *Chinese Journal of Medicinal Chemistry*, 4(2):131–136 (1994).

Partial English–language translation of Ling et al., "Synthesis of Antigenic Determinant Tyr–CGRP=(27~37) of Calcitonin Gene–Related Peptide," *Chinese Journal of Medicinal Chemistry*, 4(2):131–136 (1994).

Lowry, O.H. et al., "Protein Measurement with the Folin Phenol Reagent", *J. Biol. Chem.* 193:265–275, 1951.

Mimeault, M. et al., "Structure–Activity Study of hCGRP$_{8-37}$, a Calcitonin Gene–Related Peptide Receptor Antagonist", *J. Med. Chem.* 35:2163–2168, 1992.

Mimeault, et al., "Comparative Affinities and Antagonistic Potencies of Various Human Calcitonin Gene–Related Peptide Fragments on Calcitonin Gene–Related Peptide Receptors in Brain and Periphery", *J. Pharmacol. Exp. Ther.* 258:1084–1090, 1991.

Miyata et al., "Identification of Calcitonin Gene Related Peptide in Ovine Hypothalamic Extract", *Biochem. Biophys. Res. Commun.* 187:1474–1479, 1992.

Molina et al., "Induction of Insulin Resistance in Vivo by Amylin and Calcitonin Gene–Related Peptide", *Diabetes* 39:260–265, 1990.

Moskowitz, "Neurogenic versus vascular mechanisms of sumatriptan and ergot alkaloids in migraine", *Trends Pharmacol. Sci.* 13:307–311, 1992.

Park et al., "Somatostatin Receptors on Canine Fundic D–cells: Evidence for Autocrine Regulation of Gastric Somatostatin", *Am. J. Physiol.*, 257(2):235–241, 1989.

Poyner, D., "Calcitonin Gene–Related Peptide: Multiple Actions, Multiple Receptors", *Pharmac. Ther.* 56:23–51, 1992.

Poyner, D., "Pharmacology of receptors for calcitonin gene–related peptide and amylin", *Trends in Pharm. Sci.* 16:424–428, 1995.

Prickett, K.S. et al., "Design of Receptor Selective Peptides that Antagonize the Actions of Amylin In Vivo", *Peptides: Chemistry and Biology*, eds. Kaumaya and Hodges, Amylin Pharmaceuticals, San Diego, CA, 620–622, 1996.

Rist et al., "From Micromolar to Nanomolar Affinity: A Systemtic Approach to Identify the Binding Site of CGRP at the Human Calcitonin Gene–Related Peptide 1 Receptor", *J. Med. Chem.* 41:117–123, 1998.

Rosenfeld et al., "Production of a novel neuropeptide encoded by the calcitonin gene via tissue–specific RNA processing", *Nature* 304:129–135, 1983.

Rovero, P. et al., "CGRP Antagonist Activity of Short C–Terminal Fragments of Human αCGRP, CGRP(23–27) and CGRP(19–37)", *Peptides* 13:1025–1027, 1992.

Sakata, J. et al. "Molecular Cloning and Biological Activities of Rat Adrenomedullin, A Hypotensive Peptide", *Biochem. Biophys. Res. Commun.* 195:921–927, 1993.

Sarin, V.K. et al., "Quantative Monitoring of Solid–Phase Peptide Synthesis by the Ninhydrin Reaction", *Anal. Biochem.* 117: 147–157, 1981.

Smith, D.D. et al., "Synthesis and Biological Activity of C–Terminally Truncated Fragments of Human α–Calcitonin Gene–Related Peptide", *J. Med. Chem.* 36:2536–2541, 1993.

Steenbergh et al., "A second human calcitonin/CGRP gene", *FEBS Lett.* 183:403–407, 1985.

Tam, J.P. et al., "Mechanisms for the Removal of Benzyl Protecting Groups in Synthetic Peptides by Trifluoromethanesulfonic Acid–Trifluoroacetic Acid–Dimethyl Sulfide", *J. Am. Chem. Soc.* 108: 5242–5251, 1986.

Uren et al, "Effect of intravenous calcitonin gene related peptide on ischaemia threshold and coronary stenosis severity in humans", *Cardiovasc. Res.* 27:1477–1481, 1993.

van Rossum, et al., "Binding Profile of a Selective Calcitonin Gene–Related Peptide (CGRP) Receptor Antagonist Ligand, [$^{125}$I–Tyr]hCGRP$_{8-37}$, in Rat Brain and peripheral Tissues", *J. Pharmacol. Exp. Ther.* 269:846–853, 1994.

Westermark, P. et al., "Amyloid fibrils in human insulinoma and islets of Langerhans of the diabetic cat are derived from a neuropeptide–like protein also present in normal islet cells", *Proc. Natl. Acad. Sci. USA* 84:3881–3885, 1987.

METHODS FOR INHIBITING CGRP BINDING

This is a divisional application of Ser. No. 09/070,504, filed Apr. 30, 1998, now issued as U.S. Pat. No. 6,268,474, which is incorporated herein by reference.

This invention supported in part by NIH Grant No. HL51131. The government may have certain rights to this invention.

FIELD OF THE INVENTION

This invention relates to the field of vasoactive compounds and their antagonists. In particular, this invention relates to antagonists of the vasoactive peptide CGRP and other members of the CGRP superfamily.

BACKGROUND OF THE INVENTION

The calcitonin gene related peptide (CGRP) is a sensory neuropeptide with potent vasodilatory and cardiotonic action as described in U.S. Pat. No. 4,530,838 to Evans et al. The peptide exists in two forms (denoted α and β). α-CGRP is produced by the calcitonin gene (Amara et al. *Nature* 298:240–244, 1982 and Rosenfeld et al. *Nature* 304:129–135, 1983) while β-CGRP is the product of a separate gene (Amara et al. *Nature* 298:240–244, 1985 and Steenbergh et al. *FEBS Lett.* 183:403–407, 1985). The human β-form and α-form differ by three amino acids.

CGRP is concentrated in those areas of the body receiving sensory input from the dorsal horn with limited amounts associated with autonomic input. The peptide is present in the brain in the nuclei of sensory and motor cranial nerves and in cell bodies in the hypothalamus, preoptic area, ventromedial thalamus, hippocampus, and the like. CGRP is found in both sensory and motor nerves of the peripheral nervous system. The peptide is found in the skin, blood vessels, heart, gastrointestinal tract, tongue, esophagus, pancreas, salivary glands, lungs, kidney and other organs (Poyner, D. *Pharmac. Ther.* 56:23–51, 1992).

The release of CGRP from sensory nerve endings in inflammatory reactions can result in the local acceleration of microhemodynamic changes including vasodilation and permeability of the microcirculation resulting in plasma exudation and the release of humoral factors and inflammatory cells to the site of injury. CGRP has been used as a vasodilator in animal models of subarachnoid hemorrhage and in trials involving human subjects with congestive heart failure. CGRP administration produced hypotension associated with moderate tachycardia in hypertensive humans (Jian et al. *Chin. Med. J* 102:897–901, 1989). CGRP has also been used as a potent dilator of the coronary circulation (Ezra et al., *Eur. J Pharmacol.*, 1987). In contrast to nitrates, which have also been used as vasodilators, CGRP results in dilation by both endothelium-dependent and endothelium-independent mechanisms. Also, in contrast to nitrates, such as sodium nitroprusside, tolerance to CGRP has not been noted Bény et al. *Regul. Pept.* 25:25–36, 1989). CGRP has been demonstrated to improve the ability of patients to participate in exercise programs in patients with chronic stable angina (Uren et al. *Cardiovasc. Res.* 27:1477–1481, 1993).

CGRP has a number of problems as a therapeutic. CGRP is nonselective, inactive in oral form, generally has a short duration of action and has a number of side effects that can include uncontrolled hypotension (Feuerstein et al. *Can. J. Physiol. Pharmacol.* 73:1070–1074, 1995).

CGRP has been implicated in migraines, diabetes, sepsis and inflammation. Migraines are noted for the strength of the headache that ensues with its pathology. Most believe that the headache associated with migraines results from the profound cerebral vasodilation. CGRP containing nerve fibers innervate cerebral and dural vessels where CGRP is believed to prolong vasodilation. (Moskowitz *Trends Pharmacol. Sci.* 13:307–311, 1992). Elevated CGRP was found in the jugular vein blood of patients with migraines during a period where the patients complained of migraine symptoms, including headaches. For these reasons, CGRP antagonists have been proposed as a method for blocking cerebrovascular CGRP receptors and thus blocking the vasodilation causing migraine.

CGRP has also been postulated to be a potent indirect antagonist of insulin effects on glucose metabolism and CGRP was shown to produce insulin resistance in rat studies (Molina et al. *Diabetes* 39:260–265, 1990). For this reason CGRP has recently been implicated in Type II diabetes mellitus and to abnormalities associated with carbohydrate metabolism and hyperglycemia. CGRP has also been implicated in the hemodynamic derangements associated with endotoxemia and sepsis resulting from a variety of infectious diseases. Animals exposed to lipopolysaccharide (LPS) had elevated levels of CGRP and this coincided with hypotension and tachycardia in these animals (Joyce et al. *Surgery* 108:1097–1101, 1990 and Griffin et al. *Circ. Shock* 38:50–54, 1992).

CGRP binds to a number of different receptors, some of which have been characterized. Radioligand binding studies to assess CGRP affinity for CGRP receptors is well known in the literature (Poyner, D. R. *Pharmac. Ther.* 56:23–51, 1992). As stated in Poyner et al., a problem associated with studies to identify CGRP receptors is that lack of suitable CGRP receptor binding analogs and it is accepted that the use of CGRP antagonists is a useful way of classifying CGRP receptors. The art recognizes that there are a limited number of antagonists and that it would be desirable to have more CGRP antagonists to further classify and understand CGRP activity.

Molecules that compete for the CGRP receptor are known. These include, for example, [Tyr°]CGRP(28–37) and CGRP(8–37). Other molecules that compete for the CGRP receptor include peptides comprising the sequence of CGRP but that lack at least the first five amino acids of the CGRP amino acid sequence. [Tyr°]CGRP(28–37) was able to antagonize all forms of CGRP tested but with different potencies. Other molecules that compete for the CGRP receptor are provided elsewhere in this disclosure.

CGRP antagonists includes peptides from CGRP including amino acids 8–37 of β- CGRP (Park et al. *Am. J. Physiol.* 1989) having the amino acid sequence: VTHRLAGLLSRSGGMVKSNFVPTNVGSKAF (SEQ ID NO: 1) and peptides from α-CGRP including amino acids 8–37 and having the amino acid sequence VTHRLAGLLSRSGGMVKSNFVVPTNVGSKAF (SEQ ID NO:2) β-CGRP(8–37) has been used to counteract the effects of CGRP. For example, CGRP(8–37) has been shown to reverse the hypotension and tachycardia produced by administration of LPS to rats (Huttemeir, et al. *Am. J. Physiol.* 265:H767–H769, 1993). In addition, CGRP(8–37) has some activity against amylin (Gardiner et al. *Diabetes* 40:948–951, 1991). The affinity for CGRP(8–37) varies between tissues. For example, data indicates that the affinity of CGRP(8–37) for mesenteric artery, kidney, heart and skeletal muscle is somewhat higher than the affinity of CGRP(8–37) for adipocytes and descending colon (Poyner, D. *Trends in Pharm. Sci.* 16:424–428, 1995).

BRIEF DESCRIPTION OF THE FIGURES

FIG. 2A illustrates the antagonistic effect of h-αCGRP (8–37). The symbol □ indicates Control+h-αCGRP (8–37) ■ $3 \times 10^{-6}$ M ▲ $1 \times 10^{-5}$ M ● $3 \times 10^{-5}$ M.

SUMMARY OF THE INVENTION

Figure 1A:
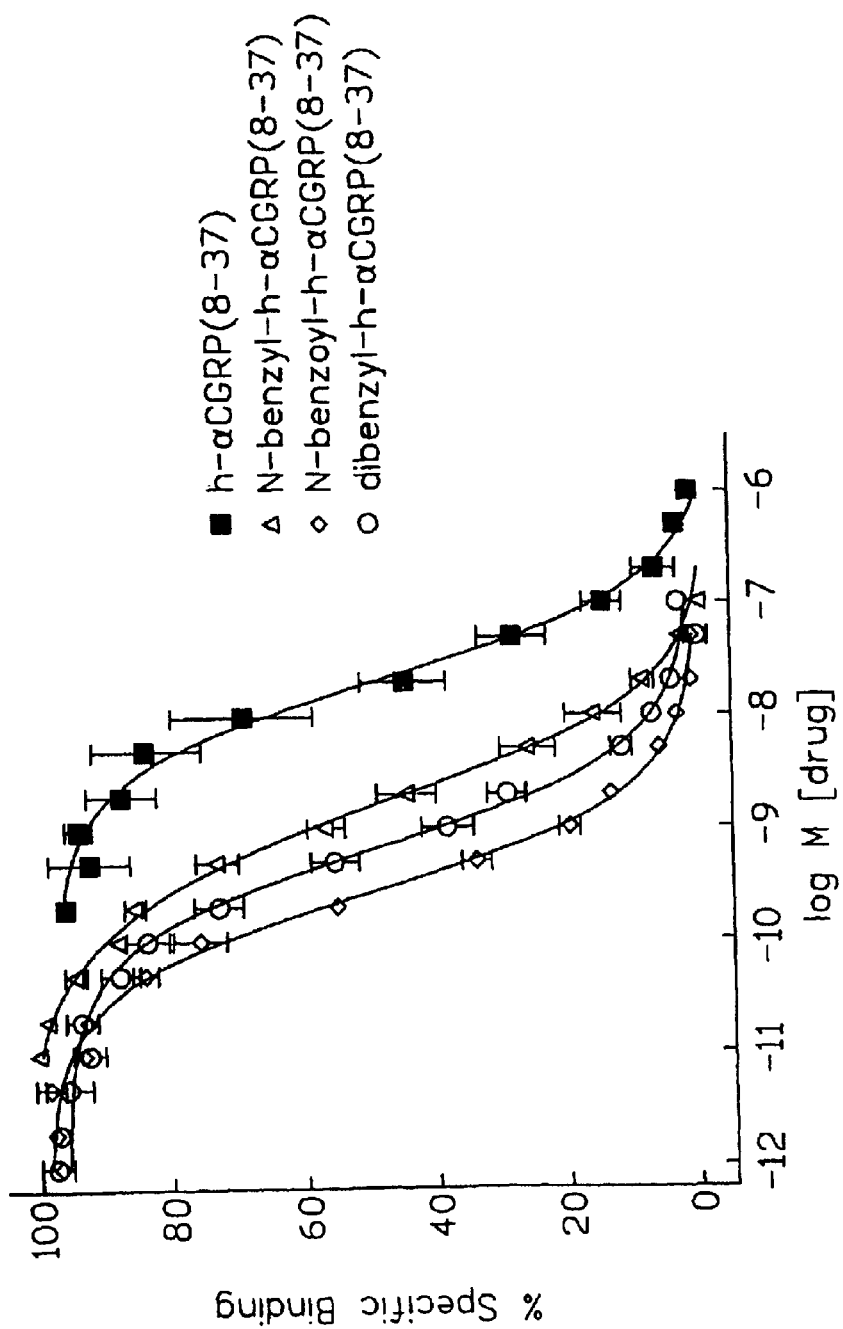
FIG. 1A is a graph demonstrating the inhibition of α-CGRP binding to coronary artery membranes in the presence of exemplary peptides, according to this invention. The symbol ■ indicates h-αCGRP (8–37) Δ N-benzyl-h-α-CGRP (8–37) ◊ N-benzoyl-h-α-CGRP (8–37) ○ dibenzyl-h-α-CGRP (8–37).

The present invention relates to vasoactive peptides having the general formula:

$$R^1-X-Z$$

wherein Z is a vasoactive peptide, R1 is an organic group, X is

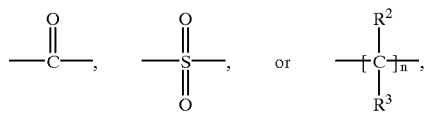

and wherein R2 and R3 are independently H or an organic group and n is a whole integer between 1 and 10.

In a preferred embodiment, Z is a peptide fragment of CGRP. In one embodiment the amino acid sequence of CGRP is SEQ ID NO:3 and in another the amino acid sequence of CGRP is SEQ ID NO:4. Preferably the CGRP is human CGRP and preferably either α-CGRP or β-CGRP. In a preferred embodiment the peptide fragment is CGRP (8–37), Tyr° CGRP(28–37), or CGRP(12–37). In another embodiment the peptide fragment is a CGRP antagonist and preferably selected from the group of peptides or peptide fragments from amylin or adrenomedullin that bind to one or more CGRP receptors. In another embodiment, the peptide fragments are peptide fragments with CGRP antagonist activity selected from CGRP receptor binding peptides preferably having at least 15 amino acids from the amino acid sequences of SEQ ID NOS:5–19.

Also preferably, $R^1$ is an aromatic group, a heterocyclic group or an alkyl group and $R^2$ and $R^3$ are independently H, an aromatic group or an alkyl group. In one embodiment, $R^1$ is a C1–C18 aromatic group, or a C1–C4 alkyl group and in another embodiment, $R^1$ is a fluoroalkyl group. In another embodiment, $R^1$ is a C5–C10 aromatic group, a C5–C9 heterocyclic group or a C1–C18 alkyl group.

Preferably $R^2$ and $R^3$ are independently H, a C1–C4 alkyl group or a phenyl moiety. Preferably, $R^2$ and $R^3$ are independently H or a C5–C10 aromatic group or a C1–C4 alkyl group.

In one embodiment, $R^1$ has the general formula:

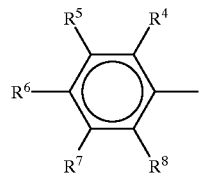

and $R^4$–$R^8$ are each independently selected from the group of H, fluoro, chloro, bromo, iodo, nitro, nitrile (cyano), amino, N-methyl amino, N,N-dimethyl amino, hydroxy, methoxy, thiomethoxy (S-methyl), methyl, ethyl, n-propyl, iso-propyl, -butyl, iso-butyl, sec-butyl, tert-butyl, trifluoromethyl, trifluoromethoxy, vinyl, acetamido, phenyl, toluyl, and methoxyphenyl. In a preferred embodiment, $R^6$ is trifluoromethyl and one or more of $R^4$, $R^5$, $R^7$ and $R^8$ is F.

In another embodiment of the invention, $R^1$ is

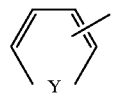

and Y is selected from the group consisting of O, NH, and S.

In yet another embodiment, $R^1$ is selected from the group consisting of:

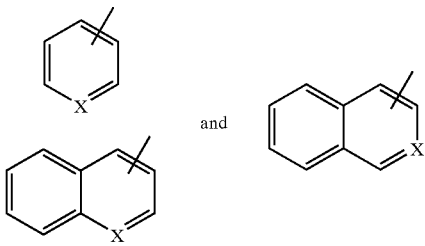

and X is C or N.

In another aspect of this invention, the peptides of this invention are selected from the group consisting of N-α-benzoyl-α-CGRP receptor antagonist peptides, N-α-benzyl-β-CGRP receptor antagonist peptides, N-α-benzoyl-β-CGRP receptor antagonist peptides, N-α-benzyl-α CGRP receptor antagonist peptides, N-α-benzyl-[(4'benzyl-His$^{10}$]-α-CGRP receptor antagonist peptides, [(4'benzyl-His$^{10}$]-β-CGRP receptor antagonist peptides, N,N-dibenzyl-α-CGRP and N,N-dibenzyl-β-CGRP.

The invention also relates to a method for inhibiting CGRP binding to one or more CGRP receptors comprising the step of contacting an effect amount of a peptide of this invention with the CGRP receptor wherein $R^1$ of the peptide is an aromatic group, a heterocyclic group or an alkyl group and $R^2$ and $R^3$ of the peptide are independently H, an aromatic group or an alkyl group. The receptor can be cell free or cell associated. The receptor can be in a cell in culture or in a cell as part of a tissue of an animal, including humans.

The invention further relates to an assay for identifying CGRP antagonists comprising the step of: combining at least one peptide of this invention and a candidate CGRP antagonist with a CGRP receptor and comparing binding of the peptide to the CGRP receptor and binding of the candidate antagonist to the CGRP receptor wherein binding of the candidate antagonist to the CGRP receptor in the presence of the peptide identifies a CGRP antagonist.

The invention also relates to a method for inhibiting CGRP activity comprising the step of administering an effective amount of a peptide of this invention to a cell wherein the cell comprises a CGRP receptor.

In yet another aspect of this invention, the invention relates to a method for identifying a CGRP receptor in a cell sample comprising the step of detecting binding of a peptide of this invention to a cell and isolating and/or characterizing the receptor.

DETAILED DESCRIPTION OF THE PREFERRED EMBODIMENTS

The present invention relates to modified peptides that serve as vasoactive peptide antagonists for the CGRP receptor. In a preferred embodiment, this invention relates to peptides with amino terminal modifications wherein the peptide functions as a CGRP antagonist.

In one embodiment, this invention relates to vasoactive peptides with the following general formula:

wherein Z is a vasoactive peptide fragment, $R^1$ is an organic group, X is

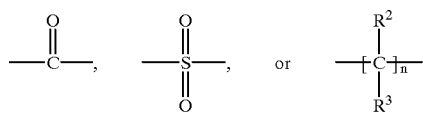

and wherein $R^2$ and $R^3$ are independently H or an organic group and n is a whole integer between 1 and 10.

The term "vasoactive peptide" refers to peptides that are capable of causing vasoconstriction or vasodilatation of blood vessels and a peptide capable of binding to a CGRP receptor refers to peptides, preferably of at least 15 amino acids in length that have CGRP receptor binding activity. For purposes of this invention, a CGRP receptor is an isolated or cell associated receptor with CGRP binding activity.

A variety of vasoactive peptides or peptide fragments that function as CGRP antagonists are known in the art and these include, but are not limited to, CGRP receptor-binding peptide fragments of CGRP, including the α and β forms of CGRP and peptides of adrenomedullin and amylin. CGRP has been isolated from a variety of animals including, but not limited to humans (β-CGRP, SEQ ID NO:3; α-CGRP; SEQ ID NO:4, Poyner, D. R. *Pharmac. Ther.* 56:23–51, 1992), rats (β-CGRP, SEQ ID NO:5; α-CGRP. SEQ ID NO:6, Poyner, supra), chickens (SEQ ID NO:7, Poyner, supra), rabbits (SEQ ID NO:8, Eysselein et al. *Peptides* 12:289–295, 1991), pigs (SEQ ID NO:9, Kimura, S. et al. *Neuropeptides* 9:75–82,1987), sheep (SEQ ID NO:10, Miyata et al. *Biochem. Biophys. Res. Commun.* 187:1474–1479, 1992), cows (SEQ ID NO:1 1 Collyear, K. et al. *J. Mol. Endocrinol.* 6:147–152, 1991), salmon (SEQ ID NO:12, Jansz, et al. *Ann. N.Y. Acad. Sci.* 657:63–69, 1992) and frogs (SEQ ID NO:13 Esneu et al. *Endocrinol.* 135:432–430,1994). Adrenomedullin has been isolated from a variety of sources including human (SEQ ID NO:14 Kitamura, K. et al. *Biochem. Biophys. Res. Commun.* 195:921–927, 1993) and rat (SEQ ID NO:15 Sakata, J. et al. *Biochem. Biophys. Res. Commun.* 195:921–927, 1993). Amylin has also been isolated from a variety of sources including, but not limited to, human (SEQ ID NO: 16 Westernark, P. et al. *Proc. Natl. Acad. Sci. USA* 84:3881–3885, 1987) and rat (SEQ ID NO:17 Leffert, J. D. et al. *Proc. Natl. Acad. Sci. USA* 86:3127–3130, 1989).

Antagonists of the CGRP receptor include a variety of peptides including peptide fragments from CGRP peptides including, but not limited to, CGRP (8–37), CGRP (28–37) including Tyr° CGRP (28–37), and CGRP (12–37). Other CGRP antagonists include h-α-CGRP (9–37), h-α-CGRP (10–37), h-α-CGRP (11–37) (Mimeault, M. et al., *J. Med Chem.* 35:2163–2168,1992). Still other CGRP antagonists include [Ala$^9$]-h-α-CGRP (8–37), [Ala$^{10}$]-h-α-CGRP (8–37), [Ala$^{11}$]-h-α-CGRP (8–37), and [Ala$^{12}$]-h-α-CGRP (8–37). Additional CGRP antagonists include h-α-CGRP (19–37), h-α-CGRP(23–37) and acetyl-h-α-CGRP(19–37) (Rovero, P. et al. *Peptides* 13:1025–1027, 1992).

Amylin antagonist peptides are known and a number of these with CGRP receptor binding activity are provided in U.S. Pat. No. 5,625,032 to Gaeta et al., and U.S. Pat. No. 5,580,953 to Albrecht et al. Preferred amylin antagonist peptides include:

human amylin (8–37)
H-ATQRLANFLVHSSNNFGAILSSTNVGSNTY-NH$_2$ (SEQ ID NO: 18),
rat-amylin(8–37)
H-ATQRLANFLVRSSNNLGPVLPPTNVGSNTY-NH$_2$) SEQ ID NO: 19),
and Acetyl-Rat-Amylin (8–37) (Deems et al. *Biochem. Biophys. Res. Commun.* 181:116–120, 1991).

Still other amnylin antagonists that can be tested for CGRP receptor binding activity include:

AC187 (SEQ ID NO:20)
(Acetyl-VLGKLSQELHKLQTYPRTNTGSNTY-NH$_2$, Beaumont et al. *Br. J. Pharmacol.* 115:713–715, 1995),
AC253 (SEQ ID NO:21)
(Acetyl-LGRLSQELHRLQTYPRTNTGSNTY-NH$_2$), and
AC625 (SEQ ID NO:22)
(Acetyl-ATQRLANELVRLQTYPRTNVGSNTY-NH$_2$ both Prickett, K. S. et al. in *Peptides Chemistry and Biology*, eds. Kaumaya, P. T. P and Hodges, S. Mayflower Scientific Ltd., Kingswinford, UK. 1996).

Preferred adrenomedullin-derived antagonists include:

h-adrenomedullin (22–52) (SEQ ID NO:23)
(TVQKLAHQIYQFTDKDKDNVAPRSKISPQGY-NH$_2$ Eguchi et al. *Endocrinol.* 135:2454–2458, 1994 and Champion et al. *Am. J Physiol.* 272:R234–242, 1997), In addition, the modifications of this invention can be incorporated into other polypeptides with vasoactivity and having CGRP receptor binding activity, such as relaxin, a molecule structurally related to amylin (Cooper et al., *Proc. Natl. Acad. Sci. USA* 85:7763–7766, 1988). Moreover, substituted peptides of amylin, CGRP or other vasoactive peptides are described in U.S. application Ser. No. 275,475.

In general, the vasoactive peptides of this invention include a carboxyamide at the C-terminus. Alternatively, the peptides of this invention can include a free carboxyl group at the terminus. Abbreviations for peptide termini are as follows: "H—" refers to a free amino group, "—OH" refers to a free carboxyl group and "—NH$_2$" refers to a carboxyamide. The term "vasoactive peptide" as used herein refers to peptides with physiological activity, particularly, but not necessarily solely, directed in activity to the vasculature system and preferably peptides with CGRP antagonist activity. In general, the peptides of this invention exhibit greater activity when a carboxyamide is positioned at the terminus of the peptide. Methods for preparing peptides with C-terminal amide groups are known in the art and, in one example, described in U.S. Pat. No. 5,503,989 to Bibbs et al.

The amino acid designations used throughout this patent application include the standard amino acid designations: A or Ala for Alanine, C or Cys for Cysteine, D or Asp for Aspartic acid, E or Glu for Glutamic acid, F or Phe for Phenylalanine, G or Gly for Glycine, H or His for Histidine, I or Ile for Isoleucine, K or Lys for Lysine, L or Leu for Leucine, M or Met for Methionine, N or Asn for Asparagine, P or Pro for Proline, Q or Gln for Glutamine, R or Arg for Arginine, S or Ser for Serine, T or Thr for Threonine, V or Val for Valine, W or Trp for Tryptophan and Y or Tyr for Tyrosine.

$R^1$ in the formnula $R^1$—X—Z is preferably an organic group. In a preferred embodiment, $R^1$ is an aromatic group, a heterocyclic group or an alkyl group. In a particularly preferred embodiment, $R^1$ is a C5–C10, a C5–C10 heterocyclic group and more preferably a C5–C9 heterocyclic group, or a C1–C18 alkyl group and more preferably a C1–C4 alkyl group. In one embodiment, $R^1$ is a fluoroalkyl.

As used herein, the term "organic group" refers to a hydrocarbon group that is classified as an aliphatic group an aromatic group, a cyclic group, or a combination of aliphatic and cyclic groups (e.g., alkaryl and aralkyl groups). In the context of the present invention, the term "aliphatic group" refers to a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" refers to an unsaturated, linear or branched hydrocarbon group with one or more carbon—carbon double bonds, such as a vinyl group. The term "alkynyl group" refers to an unsaturated, linear or branched hydrocarbon group with one or more carbon—carbon triple bonds. The term "cyclic group" refers to a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" refers to mono- or polynuclear aromatic hydrocarbon group. The term "heterocyclic group" refers to a closed ring hydrocarbon in which one or more of the atoms in the ring is an element other than carbon (e.g., nitrogen, oxygen, sulfur, etc.).

As is well understood in this technical area, a large degree of substitution is not only tolerated, but is often advisable. Substitution is anticipated on the compounds of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substitutents, such as methyl, ethyl, propyl, t-butyl, and the like, but also alkyl substitutents bearing further substituents known in the art, such as hydroxy, alkyoxy, alkylsulfonyl, halogen atoms, cyano, nitro, amino, carboxy., etc. Thus, "alkyl group" includes ether groups, haloalkyls, fluoroalkyls, nitroalkyls, carboxyalkyls, hydroxyalkyls, sufloalkyls, etc. On the other hand, the phrase "alkyl moiety" is limited to the inclusion or only pure open chain saturated hydrocarbon alkyl substitutents, such as methyl, ethyl, propyl, t-butyl, and the like.

In the vasoactive peptides of this invention, having the general formula $R^1$—X—Z, X is preferably

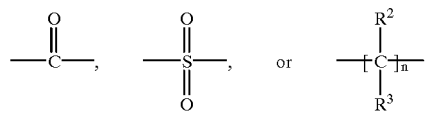

wherein $R^2$ and $R^3$ are independently H or an organic group and n is a whole integer from about 1 to about 20, preferably a whole integer from about 5 to about 20 and more preferably a whole integer from about 1 to about 4. In a preferred embodiment, $R^2$ and $R^3$ are independently H, an aromatic group, or an alkyl group and in a particularly preferred embodiment, $R^2$ and $R^3$ are independently H or a C5–C10 aromatic group or a C1–C18 alkyl group and more preferably a C1–C4 alkyl group. In yet another preferred embodiment, $R^2$ and $R^3$ are independently H, a lower alkyl moiety (e.g., about a C1–C4 alkyl) or a phenyl moiety.

In a preferred embodiment of this invention $R^1$ is an aromatic group, a heterocyclic group or an alkyl group and $R^2$ and $R^3$ are independently H, an aromatic group or an alkyl group. In one aspect of this embodiment, $R^1$ has the general formula:

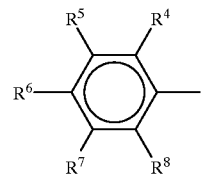

In a preferred embodiment of this invention $R^4$–$R^8$ are each independently selected from the group of H, fluoro, chloro, bromo, iodo, nitro, nitrile (cyano), amino, N-methyl amino, N,N-dimethyl amino, hydroxy, methoxy, thiomethoxy (S-methyl), methyl, ethyl, n-propyl, iso-propyl, -butyl, iso-butyl, sec-butyl, tert-butyl, trifluoromethyl, trifluoromethoxy, vinyl, acetamido, benzyl, toluyl, and methoxybenzyl. In one preferred embodiment, $R^6$ is trifluoromethyl and one or more of $R^4$, $R^5$, $R^7$ and $R^8$ are F.

In a further embodiment, $R^1$ is monocyclic, including, for example, both five-membered rings and six-member rings. A preferred five member ring with the general formula:

preferably includes Y as O, NH or S. The diagonal line extending from the center of five-membered ring and from the center of the rings of the structures depicted below indicates that the substituent —X—Z can be covalently attached to the ring at any of the carbon atoms that form the ring. In an embodiment where $R^1$ is a six-membered ring, preferably $R^1$ has the formula:

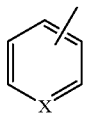

and preferably X is CH or N.

In another embodiment of this invention the invention $R^1$ is a bicyclic ring having one of the following formulas:

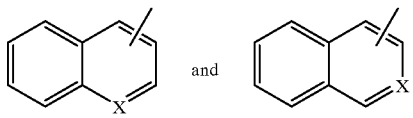

wherein X is either N or C.

Preferred peptide modifications of this invention include, but are not limited to N-α-benzyl-Z, and N-α-benzoyl-Z, wherein Z is a peptide fragment capable of binding to a CGRP receptor. Preferred benzyl analogues include, but are not limited to, N-2-furanyl-Z, N-3-furanyl-Z, N-2-pyrrolyl-Z, N-3-pyrrolyl-Z, N-2-thiophenyl-Z, N-3-thiophenyl-Z, N-2-pyridyl-Z, N-3-pyridyl-Z, N-4-pyridyl-Z, N-1-naphthyl-Z, N-2-naphthyl-Z, N-2-quinolinyl-Z, N-4-quinolinyl-Z, N-8-quinolinyl-Z, N-1-isoquinolinyl-Z, N-3-isoquinolinyl-Z, R-N-α-methylbenzyl-Z, S-N-α-methylbenzyl-Z, α,α-dimethylbenzyl-Z, N-diphenylmethyl-Z, N-trityl-Z, and [D-Phe⁰]-Z. Other preferred benzoyl analogues of the peptide fragments of this invention include, but are not limited to N-2-furanoyl-Z, N-3-furanoyl-Z, N-2-pyrroloyl-Z, N-3-pyrroloyl-Z, N-2-thiophenoyl-Z, N-3-thiophenoyl-Z, N-2-thiophenoyl-Z, N-3-thiophenoyl-Z, N-2-pyridoyl-Z, N-3-pyridoyl-Z, N-4-pyridoyl-Z, N-1-naphthoyl-Z, N-2-naphthoyl-Z, N-2-quinolinoyl-Z, N-3-quinolinoyl-Z, N-4-quinolinoyl-Z, N-8-quinolinoyl-Z, N-i-isoquinolinoyl-Z, and N-3-isoquinolinoyl-Z. Still other preferred peptide modifications of this invention include N-methanesuphonyl-Z, N-trifluoromethanesulphonyl-Z, N-benzenesulphonyl-Z, N-toluenesulphonyl-Z, N-4-methoxybenzenesulphonyl-Z, N-mesitylenesulphonyl-Z, N-4-trifluorobenzenesulphonyl-Z and N-4-trifluoromethoxybenzenesulphonyl-Z.

Preferred vasoactive peptides fragments are peptide fragments of CGRP with CGRP antagonist activity, that is the peptide fragments of this invention inhibit CGRP activity. Preferably the peptides inhibit CGRP activity by at least 25% and preferably inhibit CGRP activity by at least 50%. Particularly preferred peptide fragments of this invention are peptide fragments of α-CGRP or β-CGRP, and preferably human α-CGRP or β-CGRP. Preferred peptide fragments of CGRP include CGRP (8–37).

The peptides of this invention can be prepared using methods known in the art. Exemplary methods for preparing the peptides of this invention are provided in Example 1. For example, a number of peptides according to this invention can be assembled on MBHA resin using the methodology of Smith, D. D. et al. *J. Med. Chem.* 36:2536–2541, 1993. Those of ordinary skill in the art of peptide and protein modification can prepare the other peptide modifications of this invention without undue experimentation.

In one embodiment of this invention, the invention relates to a method for inhibiting CGRP binding to one or more CGRP receptors by contacting an effective amount of a peptide of this invention with the CGRP receptor. This method can be used in vitro, for example in assays to identify and/or isolate CGRP receptors or with intact cells either in vitro or in vivo to inhibit the effects of CGRP binding to its receptor. As an example of an assay to determine the ability of the peptides of this invention to compete with CGRP receptors, Example 2 illustrates an assay to determine whether a particular peptide modification of this invention can inhibit CGRP binding to a CGRP receptor.

Binding assays used to identify whether or not a particular peptide would inhibit CGRP binding to its receptor have been carried out using rat brain (Dennis, et al.,*J. Pharmacol. Exp. Ther.* 254:123–128, 1990, van Rossum, et al. *J. Pharmacol. Exp. Ther.* 269:846–853, 1994), spleen (Dennis, et al. *J. Pharmacol. Exp. Ther.* 254:123–128, 1990) and vas deferens (Mimeault, et al. *J. Pharmacol. Exp. Ther.* 258:1084–1090, 1991), guinea-pig atrium and vas derferens brain (Dennis, et al. *J. Pharmacol. Exp. Ther.* 254:123–128, 1990, van Rossum, et al. *J. Pharmacol. Exp. Ther.* 269:846–853, 1994), human neuroblastomer cells SK-N-MC (Rist et al. *J. Med. Chem.* 41:117–123, 1998) and pig brain, lung (Aiyar et al.*J. Neurochem.* 65:1131–1138, 1995) and kidney (Aiyar et al. *Endocrinology* 129:965–969, 1991).

Alternatively, the modified peptides of this invention, including those disclosed in the examples, can be used to identify other CGRP receptors or alternatively, the assays of the present invention can be used to test and compare the efficacy of other CGRP antagonists. For example, the $K_1$ for a specific peptide in binding to a specific type of CGRP receptor is a constant. If the $K_1$ value for the same peptide is different in one tissue compared to another tissue then this is evidence for two different receptors in these tissues.

Where the peptides of this invention are used to identify other CGRP antagonists, the peptides of this invention can be used in competition assays with candidate antagonists for example, using either labeled peptide or labeled candidate antagonist, to assess preferential binding of the receptor to a peptide of this invention or to a test antagonist. The peptides of this invention or labeled candidate antagonist can be radiolabeled, labeled with a fluorescent tag, biotinylated or otherwise tagged and/or labeled using methods known in the art.

CGRP has been implicated in a variety of diseases and pathologies as has been described in the background section of this disclosure. CGRP acts as an antagonist of insulin action and CGRP is a potent vasodilator. Activity of CGRP is mediated through binding of CGRP to one or more CGRP receptors. For purposes of this disclosure, the term CGRP-receptor superfamily refers to the class of cell receptors that bind CGRP. The CGRP antagonist, CGRP(8–37) is a known antagonist but does not appear to consistently bind strongly to one or more CGRP receptors. Exemplary peptides of this invention have demonstrated an increase in binding affinity of about 65 fold over that reported for CGRP(8–37).

CGRP receptor antagonists have been tested in vivo. For example, as indicated, CGRP(8–37) has been shown to reverse hypotension and tachycardia produced by bacterial lipopolysaccharide (LPS) administration. Therefore, this invention also relates to a therapeutically effective amount of the peptides of the present invention, preferably in a pharmaceutically acceptable buffer such as phosphate buffered solutions including saline as well as other buffered solutions well known in the art of pharmaceutical formulations that can be administered to an animal, including humans, to limit or otherwise inhibit the effects of CGRP binding to one or more CGRP receptors. The peptides can be delivered to the animal using a method that is suitable for the pathology being treated including, but not limited to, intravascular routes of delivery, parenteral routes, where applicable, intramuscular routes, or through the airways using an aerosol, a drip, or the like.

All references and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully perform the intended invention.

EXAMPLE 1

Synthesis of CGRP(8–37) Analogues

Chemicals and Materials

N-α-Butyloxycarbonyl (Boc) amino acid derivatives were purchased from Bachem (Torrence, Calif.) and Applied Biosystems (Foster City, Calif.). Reactive side chains of amino acids were protected as follows: Arg, mesitylene-2-sulphonyl; Asp, benzyl ester; Cys, p-methoxybenzyl; His, benzyloxymethyl; Lys, 2-chlorocarbobenzoxy; Ser, benzyl ether; Thr, benzyl ether; Trp, formyl; Tyr, 2-bromocarbobenzoxy. Different batches of para-methylbenzhydrylamine (p-MBHA) resin, from Applied Biosystems, were used with substitutions varying from 0.62–0.77 mmol/g. All solvents and reagents for peptide syntheses were peptide synthesis grade from Applied Biosystems and Fisher Biotechnology (Pittsburgh, Pa.). Thioanisole, ethanedithiol (EDT), m-cresol and dimethylsulfide (DMS) were purchased from Aldrich (Milwaukee, Wis.), trifluoroacetic acid (TFA) and diethyl ether were from Fisher, trifluoromethanesulfonic acid (TFMSA) was from Applied Biosystems. All chemicals were used as supplied. Analytical and semi-preparative reversed-phase high performance liquid chromatography (RP-HPLC) was performed on a Waters Corporation Inc. 625LC instrument. A VYDAC 218TP510 $C_{18}$ column (1×25 cm) supplied by the Nest Group (Southboro, Mass.) was used for semi-preparative RP-HPLC. The flow rate was 4 ml/min and the eluant was continuously monitored at 230 nm and collected in 4 ml fractions. Analytical RP-HPLC was performed on a VYDAC 218TP5415 $C_{18}$, 300 Å, column (0.46×15 cm) and a KROMASIL $C_8$, 100 Å column (0.46×25 cm). The flow rate was 1 ml/min and the eluant was continuously monitored at 220 nm. Water was obtained from a Barnstead Nanopure system and solvents for HPLC were Optima grade from Fisher. TFA for HPLC was supplied by Pierce (Rockford, Ill.). Solvents used for RP-HPLC were, Solvent A: triethylammonium phosphate (100 mM) pH 2.5; Solvent B: is a mixture of acetonitrile in Solvent A (60/40, vol/vol); Solvent C: 0.1% TFA in water; and Solvent D: 0.09% TFA in acetonitrile/water (60/40, vol/vol). Electrospray ionization mass spectrometry (ESI-MS) was performed on all samples at the Nebraska Center for Mass Spectrometry (Lincoln, Nebr.).

2. Solid Phase Peptide Synthesis of all Analogues.

All peptides were made by Merrifield's solid-phase methodology as described previously (Smith, D. D. et a; *J. Med. Chem.*36:2536–2541, 1993). N-α-Boc amino acid derivatives were coupled to p-MBHA resin (0.5 meq.) in a four-fold excess using di-isopropylcarbodiimide and hydroxybenzotriazole in N-methylpyrrolidinone. The coupling reactions were monitored by the quantitative ninhydrin test (Sarin, V. K. et al., *Anal. Biochem.* 117: 147–157, 1981).

The Boc protecting group was removed using 33% TFA in dichloromethane (DCM) for one minute and 50% TFA in DCM for 20 minutes. The first 21 amino acid derivatives were single-coupled and the last 15 amino acid derivatives were double-coupled to maintain yields in excess of 99%. After the twentieth coupling, the peptide-resin was dried and half was used for the rest of the synthesis. Once the desired sequences were assembled the N-terminal Boc group was removed as described above and portions of the peptide resin were either benzylated using benzyl bromide (10 eq.) and DIEA (10 eq.) in DCM for six hours or benzoylated using benzoic anhydride (10 eq.) and DIEA (10 eq.) in DCM for one hour. Peptides were freed of their side chain protecting groups and cleaved from the resin by the low-high TFMSA method of Tam (Tam, J. P. et al., *J. Am. Chem. Soc.* 108: 5242–5251, 1986) to yield an ether precipitated, crude product which was purified immediately.

For benzoyl derivatives and analogues, the N-terminal group can be acylated following previously described procedures (Stewart and Young in *Solid Phase Peptide Synthesis,* $2^{nd}$ edition p. 73, Pierce Chemical Co. Rockford, Ill.) using either the appropriate benzoic anhydride (10 eq.), benzoyl chloride (10 eq.) or sulphonyl chloride (10 eq.) in the presence of DIEA (10 eq.) or the appropriate benzoic acid (4 eq.) and coupling reagents such as diisopropyl carbodiimide (4 eq.) and hydroxybenzotriazole (4 eq.). The acylation reaction can be monitored using the known quantitative ninhydrin test. The benzoylated peptides can be cleaved from the resin and purified.

In one example, 2-chlorobenzyol-h-α-CGRP(8–37) is synthesized using 0.25 mmol peptide resin treated with TFA/DCM (1/1 vol/vol), washed DCM (5×1 min), mixed with DIEA/DCM (5/95 vol/vol) and washed with DCM (5×1 min). A solution of 2-chlorobenzoyl chloride (438 mg, 2.5 mmol) and DIEA (0.43 ml, 2.5 mmol) in DCM (20 ml) is mixed with the deprotected peptide-resin for 1 hour or until the acylation is complete by the quantitative ninhydrin test. The resin is then washed with DCM (5×1 min) and dried under reduced pressure. The peptide is cleaved from the resin and purified.

In another example, benzyl derivatives and analogues can be prepared by alkylating the N-terminal amino group using the appropriate benzyl halide (generally bromo or chloro compounds) (10 eq.) in the presence of DIEA (10 eq.). These reaction conditions produce a mixture of the mono-benzylated and di-benzylated peptides, that can then be cleaved from the resin and purified.

Purification of Exemplary Analogues

Analogue 1a: N-α-benzyl-h-α-CGRP (8–37) and analogue dibenzyl-h-α-CGRP(8–37). The crude product derived from benzylating 280 mg of peptide resin, was dissolved in solvent A (supra) and loaded on to the semi-preparative RP-HPLC column previously equilibrated with a mixture of solvent A and solvent B (76/24 vol/vol). The column was eluted using a linear gradient increasing solvent B composition to 54% over 75 minutes to yield two major products. Fractions containing the first product to elute from the column were pooled, diluted with an equal volume of water and loaded onto the same semi-preparative RP-HPLC column previously equilibrated with a mixture of solvent C and solvent D (67/33, vol/vol). The product was eluted from the column using a linear gradient increasing solvent D composition to 53% over 50 minutes. Fractions containing the product, as determined by analytical RP-HPLC, were pooled and lyophilized to yield 5.2 mg of a white fluffy powder. The product was >98% pure by analytical RP-HPLC. k' values under isocratic conditions and measured masses, determined by ESI-MS, are listed in Table 1.

Fractions containing the later eluting product were pooled, diluted with an equal volume of water and loaded onto the semi-preparative RP-HPLC column previously equilibrated with a mixture of solvent C and solvent D (64/36, vol/vol). This product was eluted from the column using a linear gradient increasing solvent D composition to 56% over 50 minutes. Fractions containing only the desired product, as determined by analytical RP-HPLC, were pooled and lyophilized to yield 8.5 mg of a fluffy, white powder. The product was >98% pure by analytical RP-HPLC and identified as dibenzyl-h-α-CGRP(8–37) by ESI-MS. k' values under isocratic conditions and measured masses, determined by ESI-MS, are provided in Table 1.

Analogue 1b: N-α-benzoyl-h-α-CGRP (8–37). The title compound resulting from benzoylation of 200 mg of peptide resin, was purified following the same methods described above for N-α-benzyl-h-α-CGRP (8–37). The product was eluted from the semi-preparative RP-HPLC column using a linear gradient of 31% to 51% solvent B over 50 minutes followed by a linear gradient of 35% to 55% solvent D over 50 minutes, to yield 20 mg of the desired lyophilized product (19%). k' values under isocratic conditions and measured masses, determined by ESI-MS, are listed in Table 1 (below).

Analogue 2a: N-α-benzyl-h-β-CGRP (8–37) and dibenzyl-h-β-CGRP(8–37). N-α-benzyl-h-β-CGRP (8–37) and dibenzyl-h-β-CGRP(8–37) were obtained from benzylating 200 mg of peptide resin and purified following the same methods described above for N-α-benzyl-h-α-CGRP (8–37). Both products were eluted from the semi-preparative RP-HPLC column using a linear gradient of 27% to 47% solvent B over 50 minutes. The first product to elute from the column was further purified on the semi-preparative column using a linear gradient of 31% to 51% solvent D over 50 minutes to yield 4 mg of a white fluffy powder. The product was >98% pure by analytical RP-HPLC and identified as N-α-benzyl-h-β-CGRP(8–37) by ESI-MS. k' values under isocratic conditions and measured masses, determined by ESI-MS, are listed in Table 1.

The later eluting product was further purified by semi-preparative RP-HPLC using a linear gradient of 34% to 54% solvent D over 50 minutes to yield 5.3 mg of a white, fluffy powder. The product was >98% pure by analytical RP-HPLC and identified as dibenzyl-h-β-CGRP(8–37) by ESI-MS. k' values under isocratic conditions and measured masses, determined by ESI-MS are listed in Table 1.

Analogue 2b: N-α-benzoyl-h-β-CGRP (8–37). The title compound, derived from benzoylating 200 mg of peptide resin, was purified following the same methods described above for N-α-benzoyl-h-α-CGRP (8–37). The product was eluted from the semi-preparative RP-HPLC column using a linear gradient of 32% to 52% solvent B over 50 minutes followed by a linear gradient of 36% to 56% solvent D over 50 minutes to yield 10 mg of the desired lyophilized product (10%). k' values under isocratic conditions and measured masses, determined by ESI-MS, are listed in Table 1.

TABLE 1

Physicochemical Properties of Analogues

| Peptide | ESI-MS | | Analytical RP-HPLC (k') | |
|---|---|---|---|---|
| | Calculated | Observed | [a]System 1 | [b]System 2 |
| N-α-benzyl-h-α-CGRP (8-37) | 3215.6 | 3215.6 | 0.6 | 5.6[c] |
| N-α-benzoyl-h-α-CGRP (8-37) | 3229.6 | 3229.4 | 3.3 | 7.7 |
| N-α-benzyl-h-β-CGRP (8-37) | 3221.0 | 3221.3 | 0.7 | 2.0 |
| N-α-benzoyl-h-β-CGRP (8-37) | 3233.7 | 3233.5 | 4.3 | 4.1[d] |
| Dibenzyl-h-α-CGRP (8-37) | 3305.5 | 3305.6 | 1.8 | 3.8 |
| Dibenzyl-h-β-CGRP (8-37) | 3311.1 | 3310.7 | 1.8 | 4.7 |

[a]VYDAC $C_{18}$ column (0.46 × 15 cm), 53% solvent C, 47% solvent D, 1 ml./min.
[b]KROMASIL $C_8$ column (0.46 × 25 cm), 52% solvent C, 48% solvent D, 1 ml./min.
[c]Same as [b] using 56% solvent C, 44% solvent D.
[d]Same as [b] using 50% solvent C, 50% solvent D.

EXAMPLE 2

CGRP Antagonist Testing

1. Membrane Preparations

Cell membranes were prepared from left circumflex, left anterior descending and right circumflex epicardial coronary arteries dissected from fresh pig hearts obtained from a local slaughterhouse. The arteries were cleaned of surrounding fat and connective tissue. They were cut open exposing the luminal surface and the endothelium was removed by rubbing. Arteries were then cross-cut into thin strips with a razor blade and homogenized in ice-cold 50 mM Tris-HCl buffer, pH 7.4, containing 5 mM EDTA ($Na_2$—Ca salt) using a Polytron (speed setting 5 for 20 sec). The homogenate was centrifuged at 1600 g for 10 min at 4° C. The supernatant was collected, homogenized and crude membranes pelleted by high-speed centrifugation at 50,000 g for 30 min at 4° C. The membrane pellet was reconstituted in ice cold 50 mM Tris-HCl, pH 7.4, containing 100 mM Nacl and 5 mM $MgCl_2$ and the steps of homogenization and centrifugation repeated twice as described above. The dried membrane pellet was then stored at −80° C. until use. Protein was determined according to the method of Lowry (Lowry, O. H. et al., *J. Biol. Chem.* 193:265–275, 1951)

Radioligand Binding Studies.

Crude membranes (50 μg membrane protein/tube) were incubated with varying concentrations of drugs (h-α-CGRP (8-37), N-benzyl-h-α-CGRP (8–37) or N-benzoyl h-α-CGRP (8–37)) together with 50 $pM^{125}I$-[$His^{10}$]-h-α-CGRP for 50 min at 37° C. Incubations were performed in 50 mM Tris-HCl buffer, pH 7.4 containing 5 mM $MgCl_2$, 100 mM NaCl, 0.1% (w/v) bovine serum albumin and 0.05% (w/v) bacitracin. Non-specific binding was defined as binding remaining in the presence of 1 μM h-α-CGRP. Bound $^{125}$I-h-α-CGRP was separated from free by vacuum filtration (Brandel cell harvester, model MG-48R) through glass fiber filters (Schliecher & Schuell, #32) and counted using a γ counter (LKB Wallac 1277). To reduce non-specific binding of peptides to charged surfaces, glass incubation tubes were coated with Sigmacote and glass fiber filters soaked for 60 min in 0.2% (v/v) polyethyleneimine prior to use.

We established several criteria in order for each experiment to be considered as valid data. These criteria stated that specific binding of the radiolabel was greater than or equal to 70% and that the proportion of radiolabel bound to the membrane was less than 10% of the total amount added to the incubation.

Relaxation of Pig Coronary Arteries.

The proximal portion of the left circumflex coronary artery was dissected from pig hearts at a local slaughterhouse and transported in ice-cold Krebs' solution (composition in mM; NaCl 125, KCl 5.5, $CaCl_2 \cdot 2H_2O$ 2.5, $MgCl_2 \cdot 6H_2O$ 1.2, $NaH_2PO_4$ 1.25, $NaHCO_3$ 25, dextrose 11.1, $Na_2Ca$-EDTA $2H_2O$ 0.029), equilibrated with 95% $O_2$/5% $CO_2$. Arteries were cleaned of adhering fat and connective tissue. Rings (2 mm long) were cut and mounted between two stainless-steel pins passed through the lumen of the vessel, then placed in water-jacketed organ baths maintained at 37° C. Rings were bathed in Krebs solution gassed with 95% $O_2$/5% $CO_2$, pH 7.4. One pin was connected to a Grass FT.03 force transducer for measurement of isometric tension with a Grass model 7D polygraph (Quincy, Mass.). Coronary artery rings were equilibrated at 6 g of resting tension (determined to be optimal in previous length-tension experiments by Bockman, C. S. et al., *J. Pharmacol. Exp. Ther.* 267: 1126–1133, 1993) for 30 min and then challenged twice with 45 mM KCl. To measure relaxation, tone was induced in the rings using a submaximal dose of KCl (ca. 15 mM) and when the response reached a stable degree of contractile tone, complete cumulative concentration-response relaxation curves for agonists were generated. $EC_{50}$ values (i.e., the concentration of analog needed to cause one-half of maximal relaxation) were used to quantify the potency of agonists in causing relaxation and were calculated by non-linear regression of all data points on the relaxation concentration-response curve.

Functional Determination of Antagonist Affinity Values.

To determine antagonist affinity values, coronary artery rings were prepared, equilibrated and contracted as described above. In some experiments, endogenous CGRP was depleted by incubating rings in Krebs' solution containing 100 $\mu$M capsaicin and 10 $\mu$M indomethacin for three hours. Indomethacin was added to prevent capsaicin-induced contraction of coronary arteries mediated through release of prostaglandins from the adventitia (Franc-Cereceda, A., et al. *Eur. J. Pharmacol.* 142: 235–243, 1987). Rings were then washed extensively for one hour to remove capsaicin and indomethacin. Cumulative concentration-response curves for h-α-CGRP-induced relaxation were generated in all rings, and the rings were then washed and re-equilibrated with Krebs' solution for 60 min. Control rings were incubated with Krebs solution only for 90 min followed by relaxation concentration-response curves for h-α-CGRP. No change in the potency of h-α-CGRP in causing relaxation was observed after the 90 min incubation period in control arteries. Some rings were then incubated with the antagonist, h-α-CGRP (8–37) for 90 min prior to beginning concentration-response curves for h-α-CGRP-induced relaxation. Three adjacent rings from each animal were treated with different concentrations of antagonist. For each concentration of antagonist used, dose-ratios were calculated by dividing the $EC_{50}$ value for h-α-CGRP-induced relaxation in the presence of antagonist by its $EC_{50}$ value in the absence of antagonist. Schild plots were constructed and linear regression used to determine the X-intercept ($pA_2$ value). The slopes of the Schild plots are expressed as the mean ±95% confidence limit. Differences in the slopes of Schild plots were determined by analysis of covariance. The individual $pA_2$ values were averaged and expressed as mean $K_B$ values by conversion to their antilogs.

Figure 1B:
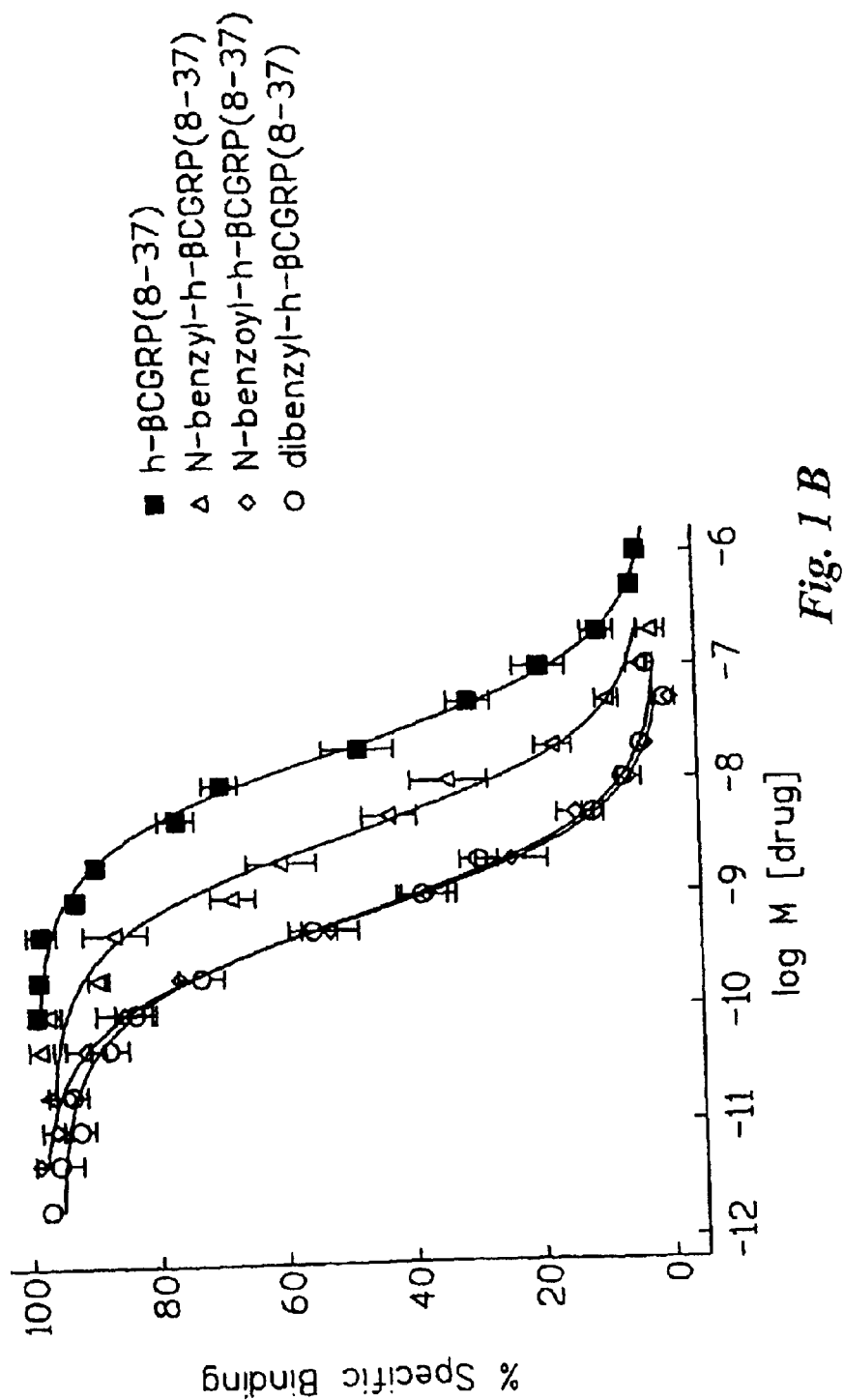
FIG. 1B is a graph showing the inhibition of CGRP binding by the βCGRP (8–37) derivatives to coronary artery membranes in the presence of exemplary peptides according to this invention. The symbol ■ indicates h-βCGRP (8–37) Δ N-benzyl-h-βCGRP (8–37) ◊ N-benzoyl-h-βCGRP (8–37) ○ dibenzyl-h-βCGRP (8–37).

The inhibition of binding of the peptides of Table 1, such as $^{125}$I-[His$^{10}$]-h-α-CGRP (1–37) binding, to membranes prepared from pig coronary arteries is shown in FIGS. 1A and 1B. Membranes were prepared from the left circumflex, left anterior descending and right circumflex coronary arteries. Competition binding experiments were performed by incubating coronary artery membranes (50 $\mu$g protein/tube) with 50 pM $^{125}$I-[His$^{10}$]-h-αCGRP and 16 different concentrations of cold ligand. Nonspecific binding was defined experimentally as the bound radioactivity remaining in the presence of 1 $\mu$M h-αCGRP or 1 $\mu$M h-βCGRP. Inhibition is expressed in the figures as percent of $^{125}$I-[His$^{10}$]-h-αCGRP binding. The potency of each of these analogs in competing for binding to CGRP receptors was determined from nonlinear regression analysis of all data points on the curve. The rank order of potency for the modified αCGRP peptides in inhibiting $^{125}$I-[His$^{10}$]-h-αCGRP from these binding sites was dibenzyl-h-αCGRP(8–37)>N-benzoyl-h-αCGRP(8–37)>N-benzyl-h-αCGRP(8–37)>H-αCGRP (8–37). The rank order of potency for the modified βCGRP peptides in inhibiting $^{125}$I-[His$^{10}$]-h-αCGRP from these binding sites was N-benzoyl-h-βCGRP(8–37)≧dibenzyl-h-βCGRP(8–37)>N-benzyl-h-βCGRP(8–37)>h-βCGRP (8–37). Each competition curve shown was the mean of 3 or 4 experiments, each using membranes prepared from different animals.

The $IC_{50}$ values for each of h-α-CGRP (8–37) modified peptides and h-β-CGRP (8–37) modified peptides are listed in Table 2 and Table 3, respectively. Since the results are similar for either the α- or β-form, only the α- will be discussed. The modified peptides possessed higher affinity than the CGRP1 receptor selective antagonist, h-α-CGRP (8–37) or h-β-CGRP (8–37). Except for N-α-benzyl-h-α-CGRP (8–37), all of these peptides were able to compete with the radioligand for binding at a single affinity site. In the case of N-α-benzyl-h-α-CGRP (8–37), This compound appeared to compete for binding to high- and low-affinity binding sites, suggesting the presence of two receptors.

Data were analyzed using non-linear least squares curve fitting (Graphpad Inplot). The concentration of unlabeled peptide required to inhibit the binding of 125I-[His$^{10}$]-CGRP from half of these sites ($IC_{50}$) was taken as the measure of affinity of each of these peptides. Non-specific binding determined using 1 $\mu$M h-α-CGRP was not different from non-specific binding determined from treating the minimum value of the competition curve as a fitted parameter. Therefore, in our analysis non-specific binding was defined by the minimum value of the competition curve. Comparisons of one- and two-site fits of binding data were made using an F-test option. In cases where P<0.05, the two-site binding model was accepted as the best fit of the data.

Figure 2:
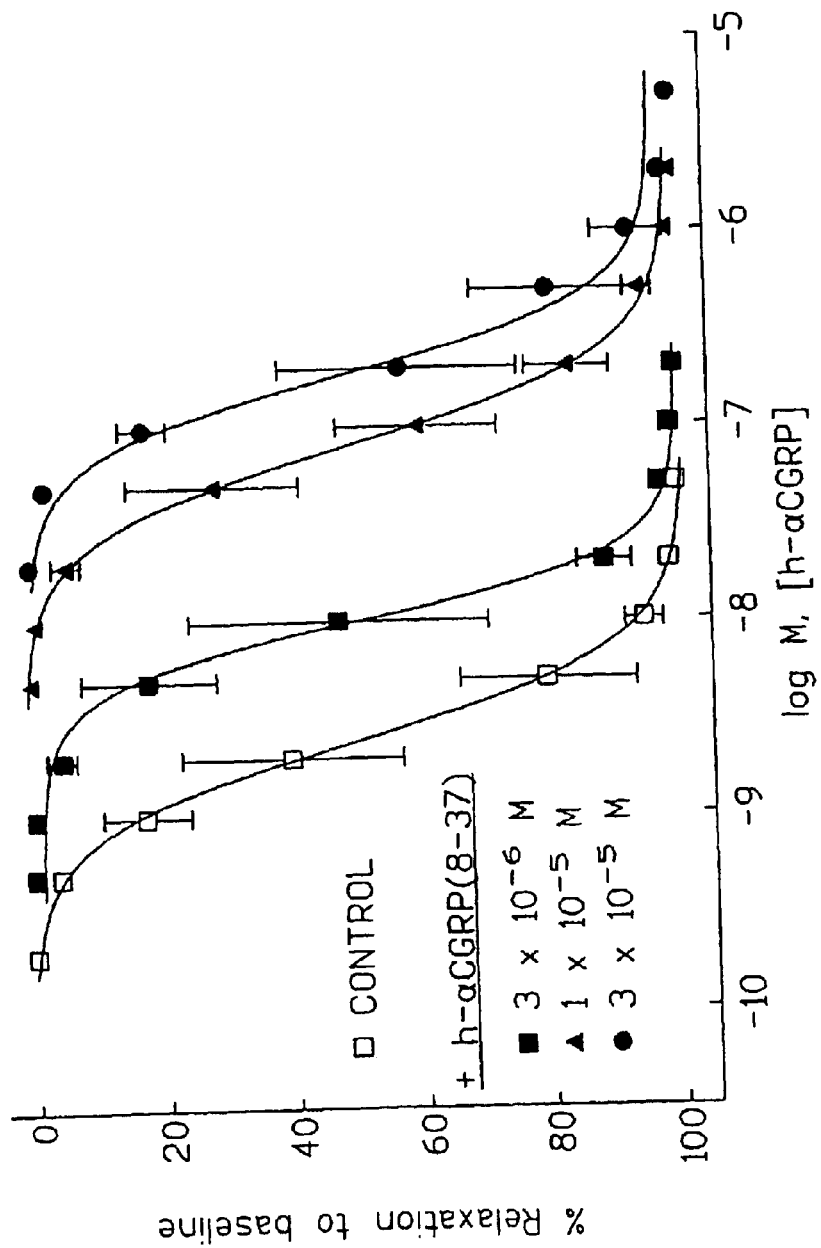
FIG. 2 illustrates the antagonist effect of αCGRP(8–37) modified peptides on h-αCGRP-induced relaxation of capsaicin-treated pig coronary artery.
Figure 2B:
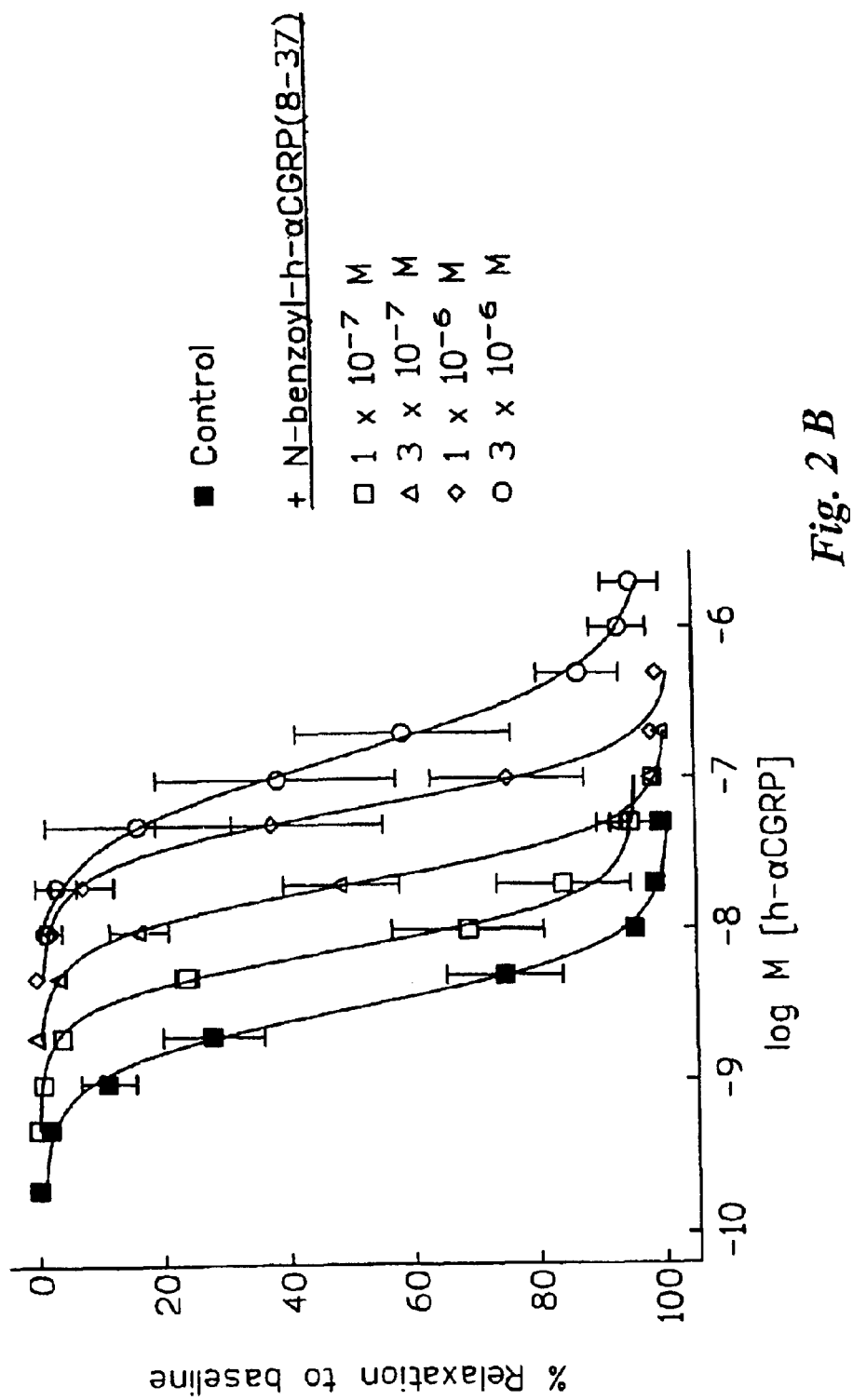
FIG. 2B illustrates the antagonistic effect of N-benzoyl-h-αCGRP(8–37). The symbol ■ indicates Control+N-benzoyl-h-αCGRP (8–37) □ $1 \times 10^{-7}$ M Δ $3 \times 10^{-7}$ M ◊ $1 \times 10^{-6}$ M ○ $3 \times 10^{-6}$ M.
Figure 2C:
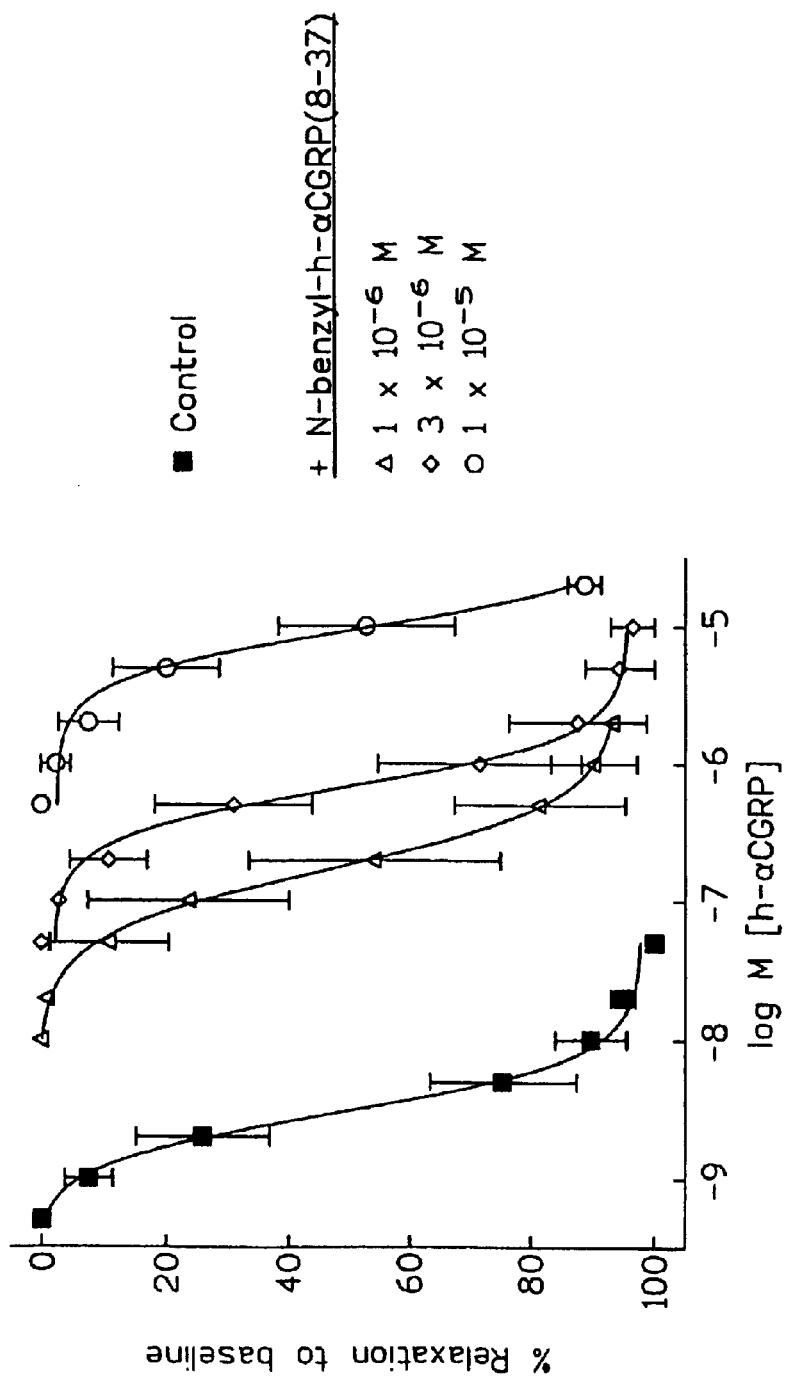
FIG. 2C illustrates the antagonistic effect of N-benzyl-h-αCGRP(8–37). The symbol ■ indicates Control+N-benzyl-h-αCGRP (8–37) Δ $1 \times 10^{-6}$ M ◊ $3 \times 10^{-6}$ M ○ $1 \times 10^{-5}$ M.
Figure 2D:
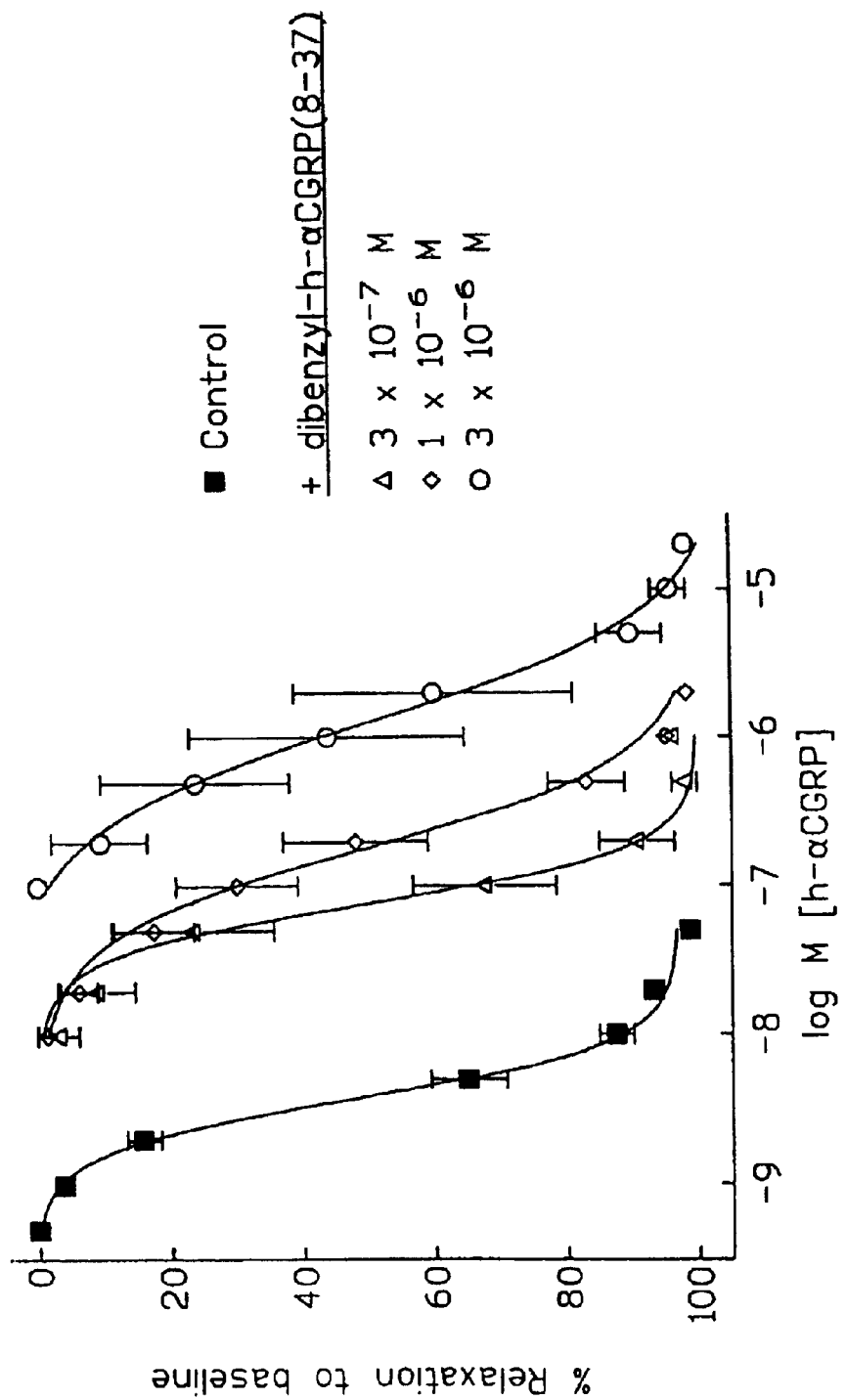
FIG. 2D illustrates the antagonistic effect of dibenzyl-h-αCGRP(8–37). The symbol ■ indicates Control+dibenzyl-h-αCGRP (8–37) Δ $3 \times 10^{-7}$ M ◊ $1 \times 10^{-6}$ M ○ $3 \times 10^{-6}$ M.

Results of the relaxation studies are illustrated in FIG. 2. As provided above, ring segments of pig left circumflex coronary artery were cleaned and mounted in glass chambered organ baths filled with Drebs-Henseleit buffer, pH 7.4 maintained at 37° C. Isometric tension on these ring segments was measured by force transducers and recorded on a polygraph. Cumulative concentration-response curves for h-αCGRP were generated on each segment in the presence and absence of antagonist. The mean concentration response curves from 4 experiments illustrating the rightwards shifts of h-αCGRP-induced relaxation caused by increasing concentrations of h-αCGRP(8–37) (FIG. 2A), N-benzoyl-h-αCGRP(8–37) (FIG. 2B), N-benzyl-αCGRP(8–37) (FIG. 2C) and dibenzyl-h-αCGRP(8–37) (FIG. 2D) are shown. The shifts of the agonist concentration-response curves produced by each concentration of the antagonist were used to calculate dose-ratio values. Linear regression analysis of these dose-ratio values plotted on a log (DR-1) vs. log [antagonist] plot was used to determine the affinity of the antagonist, denoted by the x-intercept of the regression.

N-benzyl-h-α-CGRP (8–37) and N-benzoyl-h-α-CGRP (8–37) both inhibited h-α-CGRP-induced relaxation of isolated pig coronary artery rings. Similar to h-α-CGRP (8–37), increasing concentrations of these two compounds produced increasing rightwards shifts of the h-α-CGRP concentration-response curve. Both compounds had higher affinity for the CGRP receptor in this tissue. Relative to the $K_B$ of 970 nM for h-α-CGRP (8–37), the $K_B$ for N-benzyl-h-α-CGRP (8–37) was 407 nM and the $K_B$ for N-benzoyl-h-α-CGRP (8–37) was 55 nM. Due to their higher affinity in blocking h-α-CGRP responses than CGRP(8–37), both these antagonists can replace CGRP(8–37).

TABLE 2

Radioligand Binding Data for h-α-CGRP (8-37) modified analogs

| Analogue | Affinity $IC_{50}$ (nM) | p |
|---|---|---|
| h-α-CGRP (8-37) | 14.38 ± 0.38 | |
| N-benzyl-h-α-CGRP (8-37) | 1.58 ± 0.38 | 0.004 |
| N-benzoyl-h-α-CGRP (8-37) | 0.27 ± 0.0 | <0.0001 |
| dibenzyl-h-αCGRP(8-37) | 0.22 ± 0.06 | <0.0001 |

Data was generated from 4 individual experiments, each using membranes prepared from different animals.
p value (binding): is the comparison of mean $IC_{50}$ value of analog to h-αCGRP(8-37) or h-βCGRP(8-37) by students t-test analysis. $IC_{50}$ refers to the concentration of analog that produces 50% inhibition of specific $^{125}$I-[His$^{10}$]-h-αCGRP binding from pig coronary artery membranes.

TABLE 2A

Inhibition of Relaxation for h-α-CGRP(8-37) modified analogs

| Peptide Antagonist | $K_B$ nM | p |
|---|---|---|
| h-α-CGRP (8-37) | 970.1 ± 300 | |
| N-benzyl-h-α-CGRP (8-37) | 118.7 ± 56.4 | <0.0001 |
| N-benzoyl-h-α-CGRP (8-37) | 40.36 ± 18.95 | <0.0001 |
| dibenzyl-h-αCGRP(8-37) | 29.02 ± 6.37 | <0.0001 | p value (relaxation) refers to the comparison of mean pA2 value of analog to mean pA2 value of h-αCGRP(8-37) by analysis of covariance.
$K_b$ refers to the affinity of the antagonist determined from its inhibition of h-αCGRP-induced relaxation of pig coronary artery.

TABLE 3

Radioligand Binding Data for h-β-CGRP (8-37) modified analogs

| Analogue | Affinity $IC_{50}$ (nM) | p |
|---|---|---|
| h-β-CGRP (8-37) | 20.65 ± 3.96 | |
| N-benzyl-h-β-CGRP (8-37) | 3.62 ± 0.8 | 0.0004 |
| N-benzoyl-h-β-CGRP (8-37) | 0.63 ± 0.09 | <0.0001 |
| dibenzyl-h-βCGRP(8-37) | 0.73 ± 0.14 | <0.0001 |

Data was generated from 4 individual experiments, each using membranes prepared from different animals.
p value(binding) and $IC_{50}$ are defined as above, using h-βCGRP(8-37).

EXAMPLE 3

Antagonist Testing in Rats

In vivo testing of these peptides uses anesthetized rats. A cannula is placed in the right carotid artery for measurement of blood pressure and a second cannula is placed in the left femoral vein and is used for injection of peptides into the circulation. CGRP is injected first and a reduction in blood pressure has been reported by others (Fisher et al. *Nature* 305:534–536, 1983). After blood pressure returns to normal a CGRP antagonist is given followed by a second injection of CGRP. Inhibition of the hypotensive effect of CGRP by the antagonist is evidence that the reduction in blood pressure is mediated by CGRP receptors.

While particular embodiments of the invention have been described in detail, it will be apparent to those skilled in the art that these embodiments are exemplary rather than limiting, and the true scope of the invention is that defined in the following claims.

What is claimed is:

1. A method for inhibiting CGRP binding to one or more CGRP receptors comprising contacting a CGRP receptor with a composition comprising a peptide having the general formula:

wherein Z is a CGRP receptor-binding peptide, $R^1$ is an organic group, X is

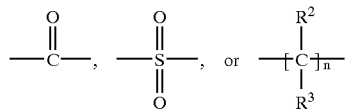

and wherein $R^2$ and $R^3$ are independently H or an organic group and n is a whole integer between 1 and 10;
in an amount effective to inhibit CGRP binding to one or more CGRP receptors.

2. The method of claim 1 wherein the CGRP receptor is on a cell.

3. The method of claim 2 wherein the cell is in culture.

4. The method of claim 2 wherein the cell is part of a tissue.

5. The method of claim 2 wherein the cell is in an animal.

6. The method of claim 5 wherein the animal is a human.

7. The method of claim 1 wherein the CGRP receptor is cell free.

8. The method of claim 1 wherein Z is a peptide fragment of at least 15 amino acids from CGRP.

9. The method of claim 8 wherein Z comprises the amino acid sequence of SEQ ID NO:1 or SEQ ID NO:2.

10. The method of claim 1 wherein Z is an antagonist of human CGRP.

11. The method of claim 1 wherein Z is an antagonist of α-CGRP or β-CGRP.

12. The method of claim 11 wherein Z comprises an amino acid sequence selected from the group consisting of SEQ ID NOS:6–17 and 23.

13. The method of claim 11 wherein Z comprises an amino acid sequence selected from the group consisting of SEQ ID NOS:18–22.

14. The method of claim 1 wherein Z is a CGRP antagonist peptide fragment selected from the group consisting of amylin, CGRP and adrenomedullin.

15. The method of claim 1 wherein $R^1$ is an aromatic group, a heterocyclic group or an alkyl group and $R^2$ and $R^3$ are independently H, an aromatic group or an alkyl group.

16. The method of claim 15 wherein $R^1$ is a C1–C4 alkyl group.

17. The method of claim 16 wherein $R^1$ is a fluoroalkyl.

18. The method of claim 16 wherein $R^2$ and $R^3$ are independently H, a C1–C4 alkyl group or a phenyl moiety.

19. The method of claim 16 wherein $R^1$ is a C5–C10 aromatic group, a C5–C9 heterocyclic group or a C1–C4 alkyl group.

20. The method of claim 19 wherein $R^2$ and $R^3$ are independently H or a C5–C10 aromatic group or a C1–C4 alkyl group.

21. The method of claim 15 wherein $R^1$ has the general formula:

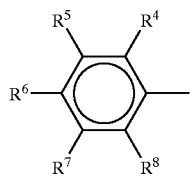

and wherein $R^4$–$R^8$ are each independently selected from the group of H, fluoro, chloro, bromo, iodo, nitro, nitrile (cyano), amino, N-methyl amino, N,N-dimethyl amino, hydroxy, methoxy, thiomethoxy (S-methyl), methyl, ethyl, n-propyl, iso-propyl, n-butyl, iso-butyl, sec-butyl, tert-butyl, trifluoromethyl, trifluoromethoxy, vinyl, acetamido, phenyl, toluyl, and methoxyphenyl.

22. The method of claim 21 wherein $R^6$ is trifluoromethyl and $R^4$, $R^5$, $R^7$ and $R^8$ are F.

23. The method of claim 21 wherein the peptide is a CGRP antagonist having at least 15 consecutive amino acids selected from a protein from the group consisting of N-α-benzoyl-α-CGRP, N-α-benzyl-β-CGRP, N-αbenzoyl-β-CGRP and N-α-benzyl-α CGRP, dibenzyl-h-α-CGRP and dibenzyl-h-β-CGRP.

24. The method of claim 15 wherein $R^1$ is

and wherein Y is selected from the group consisting of O, NH, and S.

25. The method of claim 15 wherein $R^1$ is selected from the group consisting of:

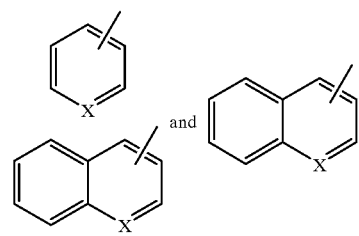

and wherein X is selected from the group consisting of C and N.

26. The method of claim 1 wherein Z is a vasoactive peptide.

27. The method of claim 26 wherein Z is an antagonist of human CGRP.

* * * * *

SEQUENCE LISTING

<160> NUMBER OF SEQ ID NOS: 23

<210> SEQ ID NO 1
<211> LENGTH: 30
<212> TYPE: PRT
<213> ORGANISM: Artificial Sequence
<220> FEATURE:
<223> OTHER INFORMATION: Artificially Synthesized Peptide

<400> SEQUENCE: 1

Val Thr His Arg Leu Ala Gly Leu Leu Ser Arg Ser Gly Gly Met Val
1               5                   10                  15

Lys Ser Asn Phe Val Pro Thr Asn Val Gly Ser Lys Ala Phe
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Artificially Synthesized Peptide

<400> SEQUENCE: 2

```
Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25              30
```

<210> SEQ ID NO 3
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 3

```
Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
            35
```

<210> SEQ ID NO 4
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 4

```
Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
            35
```

<210> SEQ ID NO 5
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 5

```
Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Lys Ala Phe
            35
```

<210> SEQ ID NO 6
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 6

```
Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30
```

Gly Ser Glu Ala Phe
            35

<210> SEQ ID NO 7
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 7

Ala Cys Asn Thr Ala Thr Cys Val Thr His Arg Leu Ala Asp Phe Leu
1               5                   10                  15

Ser Arg Ser Gly Gly Val Gly Lys Asn Asn Phe Val Pro Thr Asn Val
            20                  25                  30

Gly Ser Lys Ala Phe
            35

<210> SEQ ID NO 8
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 8

Gly Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Glu Ala Phe
            35

<210> SEQ ID NO 9
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 9

Ser Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asp Val
            20                  25                  30

Gly Ser Glu Ala Phe
            35

<210> SEQ ID NO 10
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 10

Ser Cys Asn Thr Ala Thr Cys Val Thr His Arg Leu Ala Gly Leu Leu
1               5                   10                  15

Ser Arg Ser Gly Gly Val Val Lys Ser Asn Phe Val Pro Thr Asn Val
            20                  25                  30

Gly Ser Gln Ala Phe
            35

<210> SEQ ID NO 11
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 11

```
Ser Cys Asn Thr Ala Thr Cys Val Thr His Arg Leu Ala Gly Leu Leu
1               5                   10                  15

Ser Arg Ser Gly Gly Val Val Lys Ser Asn Phe Val Pro Thr Asn Val
            20                  25                  30

Gly Ser Glu Ala Phe
        35
```

<210> SEQ ID NO 12
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 12

```
Ala Cys Asn Thr Ala Thr Cys Val Thr His Arg Leu Ala Asp Phe Leu
1               5                   10                  15

Asn Arg Ser Gly Gly Met Gly Asn Ser Asn Phe Val Pro Thr Asn Val
            20                  25                  30

Gly Ala Lys Ala Phe
        35
```

<210> SEQ ID NO 13
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 13

```
Ala Cys Asn Thr Ala Thr Cys Val Thr His Arg Leu Ala Asp Phe Leu
1               5                   10                  15

Ser Arg Ser Gly Gly Met Ala Lys Asn Asn Phe Val Pro Thr Asn Val
            20                  25                  30

Gly Ser Lys Ala Phe
        35
```

<210> SEQ ID NO 14
<211> LENGTH: 52
<212> TYPE: PRT
<213> ORGANISM: Artificial Sequence
<220> FEATURE:
<223> OTHER INFORMATION: Artificially Synthesized Peptide

<400> SEQUENCE: 14

```
Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50
```

```
<210> SEQ ID NO 15
<211> LENGTH: 50
<212> TYPE: PRT
<213> ORGANISM: Artificial Sequence
<220> FEATURE:
<223> OTHER INFORMATION: Artificially Synthesized Peptide

<400> SEQUENCE: 15

Tyr Arg Gln Ser Met Asn Gln Gly Ser Arg Ser Thr Gly Cys Arg Phe
1               5                   10                  15

Gly Thr Cys Thr Met Gln Lys Leu Ala His Gln Ile Tyr Gln Phe Thr
            20                  25                  30

Asp Lys Asp Lys Asp Gly Met Ala Pro Arg Asn Lys Ile Ser Pro Gln
        35                  40                  45

Gly Tyr
    50

<210> SEQ ID NO 16
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 16

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 17
<211> LENGTH: 37
<212> TYPE: PRT
<213> ORGANISM: Artificial Sequence
<220> FEATURE:
<223> OTHER INFORMATION: Artificially Synthesized Peptide

<400> SEQUENCE: 17

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 18
<211> LENGTH: 30
<212> TYPE: PRT
<213> ORGANISM: Artificial Sequence
<220> FEATURE:
<223> OTHER INFORMATION: Artificially Synthesized Peptide

<400> SEQUENCE: 18

Ala Thr Gln Arg Leu Ala Asn Phe Leu Val His Ser Ser Asn Asn Phe
1               5                   10                  15

Gly Ala Ile Leu Ser Ser Thr Asn Val Gly Ser Asn Thr Tyr
            20                  25                  30

<210> SEQ ID NO 19
```

```
<211> LENGTH: 30
<212> TYPE: PRT
<213> ORGANISM: Artificial Sequence
<220> FEATURE:
<223> OTHER INFORMATION: Artificially Synthesized Peptide

<400> SEQUENCE: 19

Ala Thr Gln Arg Leu Ala Asn Phe Leu Val Arg Ser Ser Asn Asn Leu
1               5                   10                  15

Gly Pro Val Leu Pro Pro Thr Asn Val Gly Ser Asn Thr Tyr
            20                  25                  30

<210> SEQ ID NO 20
<211> LENGTH: 25
<212> TYPE: PRT
<213> ORGANISM: Artificial Sequence
<220> FEATURE:
<223> OTHER INFORMATION: Artificially Synthesized Peptide

<400> SEQUENCE: 20

Val Leu Gly Lys Leu Ser Gln Glu Leu His Lys Leu Gln Thr Tyr Pro
1               5                   10                  15

Arg Thr Asn Thr Gly Ser Asn Thr Tyr
            20                  25

<210> SEQ ID NO 21
<211> LENGTH: 24
<212> TYPE: PRT
<213> ORGANISM: Artificial Sequence
<220> FEATURE:
<223> OTHER INFORMATION: Artificially Synthesized Peptide

<400> SEQUENCE: 21

Leu Gly Arg Leu Ser Gln Glu Leu His Arg Leu Gln Thr Tyr Pro Arg
1               5                   10                  15

Thr Asn Thr Gly Ser Asn Thr Tyr
            20

<210> SEQ ID NO 22
<211> LENGTH: 25
<212> TYPE: PRT
<213> ORGANISM: Artificial Sequence
<220> FEATURE:
<223> OTHER INFORMATION: Artificially Synthesized Peptide

<400> SEQUENCE: 22

Ala Thr Gln Arg Leu Ala Asn Glu Leu Val Arg Leu Gln Thr Tyr Pro
1               5                   10                  15

Arg Thr Asn Val Gly Ser Asn Thr Tyr
            20                  25

<210> SEQ ID NO 23
<211> LENGTH: 31
<212> TYPE: PRT
<213> ORGANISM: Artificial Sequence
<220> FEATURE:
<223> OTHER INFORMATION: Artificially Synthesized Peptide

<400> SEQUENCE: 23

Thr Val Gln Lys Leu Ala His Gln Ile Tyr Gln Phe Thr Asp Lys Asp
1               5                   10                  15

Lys Asp Asn Val Ala Pro Arg Ser Lys Ile Ser Pro Gln Gly Tyr
            20                  25                  30
```